United States Patent [19]

Fritzsche et al.

[11] 4,082,658

[45] Apr. 4, 1978

[54] HOLLOW FIBER MEMBRANES OF ETHYLENE COPOLYMERS AND PROCESS FOR USE

[75] Inventors: Alfred Keith Fritzsche, Cary, N.C.; Richard L. Leonard, Decatur, Ala.

[73] Assignee: Monsanto Company, St. Louis, Mo.

[21] Appl. No.: 767,096

[22] Filed: Feb. 9, 1977

[51] Int. Cl.² ...................... B01D 13/00; B01D 31/00
[52] U.S. Cl. ............................. 210/22 R; 210/23 H; 210/23 F; 210/321 R; 210/500 M; 260/2.5 R; 260/DIG. 23
[58] Field of Search .......... 210/500 M, 321 R, 321 A, 210/321 B, 23 R, 23 H, 23 F, 22 R, 22 A, 22 C, 22 D; 260/2.5 R, 2.5 AE, 2.5 AY, 2.5 AD, 2.5 H, 2.5 HA, 2.5 HB, DIG. 23

[56] References Cited

U.S. PATENT DOCUMENTS

| | | | |
|---|---|---|---|
| 3,228,877 | 1/1966 | Mahon | 210/22 |
| 3,617,546 | 11/1971 | Li et al. | 210/23 R |
| 3,925,332 | 12/1975 | Naito et al. | 260/79.3 |
| 3,931,000 | 1/1976 | Hamilton | 210/22 |
| 4,020,230 | 4/1977 | Mahoney et al. | 210/500 M |

*Primary Examiner*—Frank Sever
*Attorney, Agent, or Firm*—T. B. Leslie

[57] ABSTRACT

Hollow fiber membranes of copolymers of ethylene with 5 to 20 weight percent of copolymerizable vinyl monomers display much superior permeabilities to organic compounds than do polyethylene hollow fibers, less loss of permeability upon storage or use and good strength. Use of such new hollow fiber membranes affords an improved process for the separation of phenols from aqueous solutions thereof through permeation.

22 Claims, No Drawings

HOLLOW FIBER MEMBRANES OF ETHYLENE COPOLYMERS AND PROCESS FOR USE

BACKGROUND OF THE INVENTION

Many separations have been found to be effected by selective permeation across a thin membrane and many types of polymers have been utilized as membranes. Flat membranes as closures of cells for dialysis, reverse osmosis, and other separation processes in general have been found inefficient or expensive because of size of membranes, lack of strength, pressures withstood and the like. To meet some of these problems hollow fiber membranes have been developed, but many materials from which such hollow fibers can be spun also suffer from disadvantages of various types, including the ability to readily convert the constituent polymers into hollow fibers, having desirable properties of selective permeability and flux therethrough.

One such material, otherwise a very efficient polymer membrane for many separation uses is low density polyethylene. In flat sheet form it performs well in many uses, but when converted to hollow fibers by spinning and drawing it loses many of its advantages. For example, permeability is severely restricted by the usual and well-known spinning processes, either melt or solvent. It is theorized that this reduction occurs because of much higher crystallinity induced by the stresses of spinning and processing.

Furthermore, many of the materials from which hollow fibers are formed undergo deterioration of permeability during use and even when stored under various protective media. This deterioration of permeability adversely affects these polymer materials during periods of extended use or extended storage. For example, separations of phenols from aqueous solutions require hollow fiber membranes of a combination of properties. These include selective permeability to organic compounds such as phenols, retention of such permeability over extended periods of storage and use and reasonable strength to maintain structural integrity of the relatively thin wall hollow fibers produced.

SUMMARY OF THE INVENTION

It is an object of the present invention to provide hollow fibers which display high permeabilities to organic compounds.

Another object to this invention is to provide hollow fibers which do not suffer pronounced loss of permeability in use or storage.

A further object of this invention is to provide hollow fibers which display acceptable strengths for use in pressure processes.

Another object of this invention is to provide hollow fibers which are suitable for use in large multifiber bundles for separation processes.

Still another object of this invention is to provide an improved process for the separation of phenols from aqueous solutions thereof which utilize the hollow fibers of improved properties.

It has been found in accordance with the present invention that hollow fibers comprising copolymers of ethylene with from five to twenty weight percent of copolymerizable vinyl monomers offer a desirable combination of these improved qualities. It has been further found in accordance with this invention that an improved process for the separation of phenols from aqueous solutions thereof comprises contacting an aqueous solution of phenols with one surface of a hollow fiber membrane comprising a copolymer of ethylene and from five to twenty percent by weight of a copolymerizable vinyl monomer, maintaining a second and opposite surface of said hollow fiber membrane at a lower chemical potential than the first said surface, permeating a portion of the phenols into and through the hollow fiber membrane, and withdrawing at the second hollow fiber surface phenols having a higher concentration than the phenols concentration in the initial aqueous phenols solution.

DETAILED DESCRIPTION OF THE INVENTION

Hollow fibers which are melt-spun through extrusion dies or spinnerets and taken up on bobbins, with or without additional stretching or drawings, and are not subject to severe loss of inherent permeability by such spinning or upon storage and extended use have been found. These hollow fibers comprise copolymers of ethylene with copolymerizable vinyl monomers in which ethylene predominates. Thus, these copolymers can be converted to hollow fibers by generally the same processes by which polyethylene is converted to hollow fibers. They also find applications in the same general separations processes in which polyethylene hollow fibers have been used, particularly in the separation of organic compounds from water solution such as phenol/water solutions.

Losses in intrinsic permeability of low density polyethylene when changing from a planar film to a hollow fiber membrane have been found to be severe and range from factors of 3-10X up to 100X in the case of phenol/water separations. Similar reductions in permeability are found with other organic compound permeant systems. Consequently, compositions maintaining the good strength, processability and selectivity of low density polyethylene when extruded to form hollow fibers but which also demonstrate a good permeability rate have been sought. The ethylene copolymer compositions constituting the hollow fibers of the present invention have been found to demonstrate such a combination of high permeability and good strength as desired for use in separations processes. More particularly, they have been found to be well-suited for use in phenol/water separation processes.

Since the permeation of materials such as organic compounds across polymeric membranes is known to occur in the amorphous regions, the reduced permeabilities of hollow fibers of the same polymers, i.e. low density polyethylenes, had been attributed to increased cyrstallinity due to stress-induced crystallization from melt extrusion of such polymers to small diameters. Therefore, it is theorized that a less crystalline, more amorphous ethylene copolymer could be subjected to such melt extrusion processes and still maintain its high flux or permeability to organic compounds such as phenols.

The ethylene copolymers useful to form the fibers of the present invention comprise copolymers of about 80 to 95 percent by weight ethylene and from about 5 to about 20 weight percent of at least one copolymerizable vinyl monomer.

Examples of the copolymerizable monomers from which the copolymers useful in the present invention are formed include vinyl esters such as vinyl acetate, vinyl propionate, vinyl maleate, vinyl fumurate, and the like, acrylic and methacrylic acids, acrylic and methacrylic acid esters such as methyl acrylate, ethyl acrylate, propyl acrylate, butyl acrylate and the methyl, ethyl, propyl and butyl methacrylates, and copolymerizable mono-olefins such as propylene, N-butylene, isobutene and the like. For reasons of availability, economy and fiber production the preferred copolymerizable monomers are vinyl acetate, acrylic acid, ethyl acrylate, methyl acrylate and propylene.

The hollow fibers can be formed from these copolymers by generally the same methods and in the same equipment as homopolymeric ethylene hollow fibers have been formed. However, they exhibit very superior permeabilities and stabilities thereof when compared to polyethylene fibers similarly produced. In general the hollow fibers are produced by melt spinning through an extrusion die adapted to form a hollow fiber and quenched either in air or liquid baths, with or without additional drawing or attenuation of the fiber beyond its extruded dimension. Such processes are generally applicable to produce the hollow fibers of the present invention.

A preferred process for the production of the hollow fibers of the present invention comprises melt spinning a filtered, metered stream of molten ethylene copolymer of the above composition through a spinneret comprised of a tube within an orifice wherein the tube carries a stream of gs at a positive pressure, the extruded hollow fiber is thereafter quenched in air, an inert gas, or a liquid bath and subsequently taken up on a collecting device such as a bobbin or the like.

It has been found of advantage to delay the quenching of the extruded fiber by maintaining a heated environment about them for a brief period after their extrusion from the spinneret assembly. This has been accomplished by passing the fibers through a chimney or jacket after exiting from the spinneret for a short distance prior to their exit to air or liquid quenching, i.e. cooling. Such a chimney can take the form of a cylindrical jacket of some 6 inches to 2 feet in length, with an inside diameter equal to or larger than the diameter to the spinneret and provided with heating means adapted to maintain a wall temperature within a range from room temperature to 150° to 200° C above the operating temperature of the spinneret. Generally when the chimney is employed, the wall temperature is maintained somewhat above that of the operating temperature of the heated spinneret, i.e. from about 10° to 100° C above the spinneret temperature.

After exiting from the chimney the fibers are quenched or cooled by passage through an area of ambient room temperature air for a sufficient distance to cool and thoroughly solidify the hollow fibers. For some fibers it has been found of value to initially quench in ambient air and complete their cooling in a liquid bath comprised of an inert liquid, generally water. The liquid can be kept at room temperature, below or above as indicated to achieve the final fiber temperature desired. If desired, a finish or other application can be applied to the fiber after quenching and prior to collecting same on a collecting device. Any desired subsequent treatment or conditioning of the hollow fibers can generally conveniently be carried out while the hollow fibers are wound on the collecting device.

The size and wall thickness of the hollow fibers produced can be controlled in several ways. Initially, the size of the orifice, tube and inert gas pressure selected will govern the size of fibers produced, as modified by the degree of enlargement of fiber dimensions by release from the metered pressure of extrusion through the spinneret. Size and wall thickness can be varied by varying the pressure of extrusion through the spinneret and the take-up speed at which the fibers are drawn away from the spinneret. Changes in one of these values can be compensated for by changes in the other. Once solidification has been achieved, it is possible to subject the hollow fibers to additional stretching or drawing to reduce the wall thickness thereof but such procedures are generally not preferred because of the additional crystallization of the polymers thereby induced.

The hollow fibers can be produced in a variety of sizes and wall thicknesses. Generally, it has been found that useful permeabilities can be attained with a fiber wall thickness of from about 10 to 150 microns, and more preferably from about 15 to 100 microns. In hollow fibers the measurement of wall thickness is facilitated by determining the outside diameter and inside diameter of the fiber and taking as the wall thickness one half of the difference in these diameters. Hollow fibers of various sizes can be produced without exceeding the above desired wall thicknesses by enlarging the diameter of the inner bore contemporaneously with spinning of hollow fibers of larger outside diameter. Thus, a fiber of 600 OD/400 ID has a wall thickness of 100, the same as a fiber of 250 OD/50 ID. Fibers with outside diameters of from 50 to 1000 microns and wall thicknesses in ratios to said outside diameter of from 0.1 to 0.4 can be readily produced from such ethylene copolymers.

Permeabilities of hollow fibers can be stated in a number of ways. Two meaningful measurements are the intrinsic permeability P, stated in units cc-cm/cm$^2$-sec ($\Delta$VF), and is derived from the equation:

(1) $P = 1 \, P_A$ where 1 is film thickness.

$P_A$ or net permeation, the other meaningful figure, is derived from the equation:

(2) $J_{ID\,basis} = P_A \Delta VF$ where J is the observed flux in cc/cm$^2$-sec and $\Delta$VF is the volume fraction difference.

Thus, P for a hollow fiber can be taken as:

(3) $P = P_A (ID/2) \log_n (OD/ID)$ where $P_A$ is $J_{ID\,basis}/\Delta VF$

Polyethylene membranes have been found to exhibit intrinsic permeabilities P for phenol from a phenol/water solution of from 2 to 10 $\times$ 10$^{-8}$ cc-cm/cm$^2$-sec $\Delta$VF as flat sheets. However, polyethylene when melt extruded into the form of hollow fibers does not maintain these values, but usually demonstrates an intrinsic permeability P in the range of about 0.2 to about 2.0 $\times$ 10$^{-8}$. Likewise, the value for net permeability $P_A$ for phenol of about 0.5 to about 2.5 and generally about 1.0 $\times$ 10$^{-4}$ cc/cm$^2$-sec $\Delta$VF, desired for potential commercially economical separations of phenol/water solutions, was not found with polyethylene hollow fibers, but, on the contrary, such values for $P_A$ ranged from about 0.02 to 0.2 $\times$ 10$^{-4}$ only. Consequently, hollow fibers of polyethylene have not been found to demonstrate commercially acceptable rates of permeation for use in the phenol/water solutions separation.

It has now been found that the ethylene copolymer hollow fibers of the present invention comprising copolymers of ethylene with from 5 to 20% by weight of copolymerizable vinyl monomers demonstrate intrinsic permeabilities P for phenol from a phenol/water solution ranging from about 5 to 75 $\times$ 10$^{-8}$ and as high as 100 $\times$ 10$^{-8}$. Likewise, the ethylene copolymer hollow fibers of the present invention demonstrate net permeabilities $P_A$ for phenol ranging from about 0.25 to 4.0 × $10^{-4}$ cc/cm²-sec ΔVF. Thus, the hollow fibers of this invention have uniformly been found to be superior, and generally superior by an order of magnitude or more on the average to the hollow fibers extruded by the same procedures from polyethylene homopolymers.

Among the further disadvantages of the use of polyethylene hollow fibers is the fact that such polyethylene hollow fibers demonstrate a severe deterioration in permeation rates upon aging in storage or use. This deterioration in measured permeabilities occurs at a very rapid rate in unannealed hollow fibers, i.e. a fourfold decrease in 50 hours even when stored under a phenol/water solution at operating temperatures of 70° C. Although preannealed fibers demonstrate a slower rate of decline, there is still a precipitous decline in their measured intrinsic permeability P, i.e. 100% in 120 hours storage. In contrast the hollow fibers of this invention demonstrate no such rapid loss in intrinsic permeability showing approximately a 40% decline which stabilizes after a period of 48–96 hours. In the case of the ethylene/propylene copolymer hollow fibers there has been found an increase in P of some 40-50% in like periods of storage. Hence, the hollow fibers of the present invention demonstrate a distinct advantage in maintaining useful permeabilities in storage and use over those produced from ethylene homopolymers.

The hollow fibers of the present invention have also been found to demonstrate acceptable strength properties under operational conditions. The yield stress ($\sigma_y$) and elastic modulus (E × $10^{-8}$) have been determined under conditions approximating those of use, i.e. at elevated temperatures and in a phenol/water solution, and have been found to maintain levels acceptable for use in separations processes.

The hollow fibers of the present invention are useful in carrying out separations processes, particularly for organic compounds, and more particularly for such compounds from aqueous solutions and mixtures. One preferred use of these hollow fibers is in the separation of phenols from water solutions thereof. Such separations are carried out by contacting one side of such hollow fiber membranes with an aqueous solution of phenols while maintaining on the opposite side of said hollow fiber a lower chemical potential than the first side and withdrawing from said opposite side phenols at a higher concentration than in said aqueous contacting solution. Such lower chemical potential can be produced by maintaining a lower pressure on the second or opposite side sufficient to vaporize said phenols, by contacting said second or opposite side with a solvent for phenols permitting a higher concentration of phenols than in said contacting aqueous solution, or by contacting said second or opposite side with a solution of a complexing agent or reagent which will react with said phenols to produce compounds of phenols such as salts. This latter is the most preferred method of operation. It offers a facile method for producing desired compounds of phenols and/or regenerating the phenols if desired.

In order for phenols to permeate the ethylene copolymer hollow fiber membranes the phenols must be in undissociated form, i.e. acid form. To ensure that such acid form of the phenols is present the aqueous solutions of phenols must have a pH of less than 8.0 and most preferably less than 5.0. Consequently it is generally preferred to adjust the pH of the aqueous solution of phenols with an acid such as hydrochloric acid to pH of 5.0 or below. Other organic compounds which can be separated from aqueous solutions such as carboxylic acids, organic amines and the like, may require adjustment of the pH depending upon the dissociation constants of the specific compounds.

The complexing agents or reagents are selected from those which in solution will permit a higher concentration of phenolic bodies on the permeate side than on the feed or permeant side of the hollow fibers. Complexing agents can be selected from organic amines such as alkylamines and alkanolamines and the like. Reagents which react to form compounds of phenols include alkali metal, alkaline earth metal, ammonium and other hydroxides which readily react to produce phenates in water and other polar solvents. Preferred reagent solutions are aqueous solutions of alkali metal hydroxides such as sodium hydroxide, potassium hydroxide and the like. It is preferred to maintain the pH of the solutions of permeated phenols at about 10 or more to insure the phenate form is maintained. Such solutions are readily circulated through or about the hollow fibers to maintain fresh reagent in contact with said permeate side of the hollow fibers. The hollow fibers of the present invention have been found to be resistant to such complexing agent or reagent solutions and not to be swelled or weakened by contact therewith.

The preferred method of utilizing the hollow fibers in a phenols/water separation process is assemblies of such fibers which present large surface areas for the permeation of the phenols. The groups of hollow fibers can be assembled in any desired manner that provides for isolating the feed or permeant aqueous phenols solution on one surface of the fibers and the complexing or reagent solution sweep on the opposite surface thereof. One convenient method of assembly that provides a large number of such fibers and a consequent large surface area for contact and permeation is assembly into a hollow fiber module comprising an array of fibers of selected length provided with tube sheets or seals adjacent each end thereof to maintain the position of each fiber and constitute manifolds for passage of fluids such as a complexing or reagent solution through the bores of the hollow fibers. A cover or shell about the fiber bundle sealed to both the tube sheets or seals provides the manifolding function for a different fluid such as a feed stream of aqueous phenol solution. Either the feed stream or the reagent solution can be passed through the bore or about the outside of the assembled hollow fibers as desired.

It is sometimes desirable to pretreat the hollow fibers prior to their use in the intended separation processes. For example, it has sometimes been found advantageous to anneal the fibers by heating, either in an oven or in a heated liquid bath, for periods sufficiently long to relax all strains which may have developed in the fibers by the production thereof. Generally, a period of from one to four hours of such annealing treatment are desirable. It has also been found beneficial in many cases to store the fibers under liquids for various periods prior to their assembly and use. Such storage can be accomplished with the fibers on the collecting device or bobbin, as a secured bundle of cut fibers or after assembly into a module.

When applied to various aqueous feed streams containing phenols, particularly when such streams represent waste streams from one or more industrial processes it is frequently essential to treat such waste streams, depending upon their composition, to prepare the streams to contact the separations unit comprising the hollow fiber membranes. Filtration of such streams is often necessary to eliminate any traces of solids which might become blind or plug the fibers. Adjustment of the pH of the streams is often required and may result in formation of separate phases requiring removal before utilizing the stream in a separation step or unit. Other components of the aqueous feed streams may require separation by other means if found deleterious to the hollow fiber membranes or any part of an assembled module. Such treatment of the aqueous phenols feed streams form no part of the present invention.

The advantages and applications of the hollow fibers of the present invention are illustrated in the following examples in which all parts are by weight unless otherwise specified.

In all the examples which follow the hollow fibers were produced by melt spinning using conventional techniques. A Brabender ¾ inch extruder was used. Pellets of a selected polymer or copolymer were fed into the feed zone of the extruder by gravity. The extruder was provided with a metering pump to control the melt pressure on the spinneret assembly. The temperatures of the feed zone, metering, mixing and melt zones of the extruder were controlled by separate jacket sections. The spinneret assemblies were of the tube-in-orifice type with the tube supplied with a source of low pressure inert gas, i.e. nitrogen, with the pressure controlled to a preselected value. The temperature of the spinneret assembly was controlled by a separate electrically heated jacket and a constant temperature maintained as indicated by a thermocouple in the spinneret assembly. An adjustable feed take up device collected the filaments. In those runs where use of a chimney is indicated the chimney consisted of an electrically heated metal jacket of inside diameter the same as the outside diameter of the spinneret and of 6 inch or 10 inch length with the wall temperature controlled to a preselected constant temperature. Where air quench is indicated ambient air was the only quenching medium. Where a water quench is indicated initial quenching occurred in air for several inches and thereafter the filaments were passed through a water bath at room temperature.

Initial net permeability and intrinsic permeability to phenol were determined for each reported fiber by assembling a skein of 60 fibers in a loop through a sealed rubber stopper and providing the respective ends with a nipple to pass fluids through the fiber bores. The looped skein of fibers was immersed in aqueous phenol solutions at the temperature indicated and the selected bore fluid, generally a 30% solution of sodium hydroxide in water, was passed through the fiber bores. The exiting bore fluid was collected, diluted to a given volume and the concentration of sodium phenate present in the effluent determined by absorption of ultraviolet light at 287 mµ. The amount of phenol permeated through the hollow fiber membranes was calculated from the concentration of sodium phenate and the time of the test, generally 20 to 30 minutes.

EXAMPLE 1

In Table I there are set out the conditions of melt spinning and conditioning as well as the results of testing for intrinsic permeabilities (P) and net permeabilities ($P_A$) of a series of hollow fibers composed of homopolymeric low density polyethylenes. The melt indices of these polyethylenes varied from 0.6 to 55 while the melt temperatures, spinneret temperatures, use of a chimney, quench media and take up speeds were varied as shown. The dimensions of the hollow polyethylene fibers produced also varied with IDs from 40 to 75 microns and wall thicknesses, as indicated by (OD-ID)/2 of from 12.5 to 35 microns. It will be observed that the intrinsic permeabilities of the polyethylene hollow fibers as measured in a 3% by weight solution of phenol in water at 70° C ranged from a P × $10^8$ of about 0.1 to 4.3, while the net permeabilities $P_A$ × $10^4$ ranged from 0.03 to 0.22.

TABLE I

Hollow Fibers Spun from Low Density Polyethylene

| Spin No. | 1 | 2 | 3 | 4 | 5[a] | 6 |
|---|---|---|---|---|---|---|
| Melt Index | 55 | 55 | 55 | 30 | 2.65 | 2.65 |
| Melt Temperature (° C) | 225 | 200 | 225 | 225 | 320 | 325 |
| Chimney Temp. (° C) | — | — | 225 | 250 | — | — |
| Quench Conditions (at Room Temperature) | air | water | water | water | air | water |
| Take-up Speed, mpm | 305 | 230 | 230 | 230 | 238 | 238 |
| Fiber Dimensions: | | | | | | |
| OD, microns | 85 | 110 | 105 | 109 | 114 | 110 |
| ID, microns | 55 | 66 | 62 | 62 | 57 | 40 |
| Initial $P_A$(70° C) × $10^{4b}$ | .01 | .13 | .06 | .06 | .22 | .015 |
| Initial P (70° C) × $10^{8c}$ | .12 | 2.2 | 1.0 | 1.0 | 4.3 | .3 |

| Spin No. | 7 | 8[a] |
|---|---|---|
| Melt Index | .6 | .6 |
| Melt Temperature (° C) | 350 | 350 |
| Chimney Temp. (° C) | 360 | 360 |
| Quench Conditions at Room Temperature | air | air |
| Take-up Speed, mpm | 127 | 128 |
| Fiber Dimensions: | | |
| OD, microns | 100 | 100 |
| ID, microns | 75 | 75 |
| Initial $P_A$(70° C) × $10^{4b}$ | .03 | .13 |
| Initial P (70° C) × $10^{8c}$ | .44 | 1.9 |

[a]Annealed 2 hours in oven at 80° C at constant length prior to test.
[b]$P_A$ is calculated according to the relation $J_{ID\ basis} = P_A \Delta v$, where J is the observed flux in cc/cm$^2$-sec and $\Delta v$ is the volume fraction driving force for phenol, calculated from measured ppm assuming unit phenol density.
[c]P in cc-cm/sec-cm$^2$- $\Delta v$ from the equation for fibers: $P = P_A(ID/2) \ln(OD/ID)$, where $P_A = J_{fiber_{ID\ basis}}/\Delta v$.

EXAMPLE 2

In Table II there are set out the varied conditions of melt spinning and test results for some 14 different hollow fibers produced from copolymers of ethylene and vinyl acetate with varied vinyl acetate contents. The dimensions of these fibers varied in OD from 100 to 190 microns and in wall thickness from 18 to 60 microns. All the copolymer hollow fibers were preannealed above their use temperature, i.e. at about 70°-80° C., for two hours unrestrained prior to testing them. Table II shows that both the net permeabilities $P_A$ × $10^4$ and intrinsic permeabilities P × $10^8$ are far superior to those found with the ethylene hollow fibers set out in Table I, and generally about an order of magnitude superior thereto.

TABLE II

Hollow Fibers Spun from Ethylene-Vinyl Acetate

| Spin No. | 9 | 10 | 11 | 12 | 13 | 14 |
|---|---|---|---|---|---|---|
| Melt Index | 3.0 | 3.0 | 3.0 | 2.5 | 2.5 | 12 |
| % Ethylene | 90 | 90 | 90 | 88 | 88 | 88 |
| % Vinyl Acetate | 10 | 10 | 10 | 12 | 12 | 12 |
| Melt Temperature (° C) | 200 | 280 | 295 | 290 | 250 | 240 |
| Chimney Temp. (° C) | — | 300 | — | — | — | — |
| Quench Conditions (Room Temperature) | air | water | air | air | air | air |
| Take-up Speed, mpm | 55 | 119 | 67.5 | 61 | 82 | 342 |
| Fiber Dimensions: | | | | | | |
| OD, microns | 190 | 180 | 130 | 290 | 185 | 100 |
| ID, microns | 105 | 100 | 60 | 170 | 103 | 65 |
| Initial $P_A$ × $10^{4a}$ | 1.4 | 1.1 | 1.6 | 1.4 | 3.0 | 1.9 |
| Initial P × $10^{8b}$ | 43 | 34 | 74 | 63 | 91 | 28 |
| Temp. of P and $P_A$ | 70 | 70 | 70 | 70 | 70 | 70 |

TABLE II-continued

Hollow Fibers Spun from Ethylene-Vinyl Acetate

| Measurement Spin No. | 15 | 16 | 17 | 18 | 19 |
|---|---|---|---|---|---|
| Melt Index | 12 | 12 | 18 | 18 | 18 |
| % Ethylene | 88 | 88 | 82 | 82 | 82 |
| % Vinyl Acetate | 12 | 12 | 18 | 18 | 18 |
| Melt Temperature (° C) | 290 | 290 | 185 | 185 | 185 |
| Chimney Temp. (° C) | — | — | 190 | 190 | 190 |
| Quench Conditions (Room Temperature) | air | water | air | air | air |
| Take-up Speed, mpm | 188 | 188 | 345 | 345 | 268 |
| Fiber Dimensions: | | | | | |
| OD, Microns | 150 | 190 | 102 | 123 | 148 |
| ID, microns | 90 | 95 | 62 | 68 | 95 |
| Initial $P_A \times 10^{4a}$ | 2.9 | 2.4 | 1.9 | 1.6 | 1.7 |
| Initial $P \times 10^{8b}$ | 67 | 79 | 30 | 30 | 34 |
| Temp. of P and $P_A$ Measurement | 70 | 70 | 50 | 50 | 50 |

| Spin No. | 20 | 21 | 22 |
|---|---|---|---|
| Melt Index | 8.0 | 8.0 | 2.5 |
| % Ethylene | 82 | 82 | 82 |
| % Vinyl Acetate | 18 | 18 | 18 |
| Melt Temperature (° C) | 290 | 290 | 238 |
| Chimney Temp. (° C) | 70 | 70 | — |
| Quench Conditions (Room Temperature) | air | air | water |
| Take-up Speed, mpm | 289 | 231 | 270 |
| Fiber Dimensions: | | | |
| OD, microns | 123 | 136 | 150 |
| ID, microns | 61 | 95 | 92 |
| Initial $P_A \times 10^{4a}$ | 1.9 | 2.5 | 2.2 |
| Initial $P \times 10^{8b}$ | 41 | 56 | 45 |
| Temp. of P and $P_A$ Measurement | 60 | 60 | 60 |

$^a P_A$ is calculated according to the relation $J_{ID\,basis} = P_A \Delta v$, where J is the observed flux in cc/cm$^2$-sec and $\Delta v$ is the volume fraction driving force for phenol, calculated from measured ppm assuming unit phenol density.

$^b$P is cc-cm/sec-cm$^2$- $\Delta v$ from the equations for fibers: $P = P_A(ID/2) \ln (OD/ID)$, where $P_A = J_{fiber, ID\,basis}/\Delta v$.

EXAMPLE 3

In Table III there are set out the conditions of melt spinning and the test results for samples of hollow fibers produced from ethylene-acrylic acid copolymers with varied contents of acrylic acid. The hollow fiber dimensions varied from OD of 95 to 155 microns and in wall thickness from 10 to 33 microns. All hollow fibers were preannealed for two hours unrestrained at 70° C or 80° C. Table III demonstrates that the ethylene-acrylic acid copolymer hollow fibers were superior to those of ethylene homopolymers in both $P_A$ and P.

TABLE III

Hollow Fibers Spun from Ethylene-Acrylic Acid

| Spin No. | 23 | 24$^a$ | 25 | 26$^a$ | 27 | 28 | 29 |
|---|---|---|---|---|---|---|---|
| Melt Index | 5.5 | 5.5 | 9.0 | 9.0 | 6.0 | 6.0 | 40 |
| % Ethylene | 92 | 92 | 92 | 92 | 88 | 88 | 85 |
| % Acrylic Acid | 8 | 8 | 8 | 8 | 12 | 12 | 15 |
| Melt Temperature (° C) | 230 | 245 | 240 | 240 | 245 | 245 | 180 |
| Chimney Temp. (° C) | — | 120 | — | 100 | 200 | 140 | — |
| Quench Conditions (Room Temperature) | air | air | air | air | air | air | air |
| Take-up Speed, mpm | 22— | 285 | 346 | 346 | 346 | 346 | 346 |
| Fiber Dimensions: | | | | | | | |
| OD, microns | 140 | 155 | 135 | 95 | 95 | 104 | 105 |
| ID, microns | 75 | 100 | 75 | 47 | 75 | 57 | 60 |
| Initial $P_A$ (70° C) $\times 10^4$ | 0.40 | 1.1 | 0.25 | 1.3 | 1.5 | 1.4 | 0.4 |
| Initial P (70° ) $\times 10^8$ | 11 | 27 | 6 | 21 | 25 | 24 | 8 |

$^a$Samples annealed 1 hr. unrestrained in water bath at 80° C, all the others were annealed 1 hr. unrestrained in water bath at 70° C prior to use.

EXAMPLES 4 AND 5

Table IV and V set out, respectively, the spinning conditions and test results found with hollow fibers produced from copolymers of ethylene and ethyl acrylate and from an ethylene-propylene copolymer thermoplastic rubber. In every case the intrinsic permeability was far superior to that for ethylene homopolymer hollow fibers. In the instance of the ethylene propylene copolymer rubber its inherent elasticity produced hollow fibers both larger and with thicker walls than the ethylene hollow fibers of Table I. Therefore, the ethylene propylene hollow fiber of Table V was quite superior in $P_A$ considering that its wall thickness of 142 microns was from 4 to 10 times the thickness of the ethylene fibers in Table I.

TABLE IV

Hollow Fibers Spun from Ethylene Ethyl Acrylate$^a$

| Spin No. | 30 | 31 | 32 |
|---|---|---|---|
| Melt Index | 8 | 8 | 1.5 |
| % Ethyl Acrylate | 8 | 8 | 15 |
| Melt Temperature (° C) | 220 | 220 | 200 |
| Chimney Temp. (° C) | — | — | 360 |
| Quench Conditions (Room Temperature) | water | water | air |
| Take-up Speed, mpm | 163 | 155 | 284 |
| Fiber Dimensions: | | | |
| OD, microns | 150 | 150 | 151 |
| ID, microns | 100 | 100 | 96 |
| Initial $P_A$ (70° C) $\times 10^4$ | 1.3 | 0.8 | 2.7 |
| Initial P (70° C) $\times 10^8$ | 27 | 23 | 59 |

$^a$These samples were preannealed for one hour at 80° C in water prior to the test.

TABLE V

Hollow Fibers Spun from Ethylene Propylene Thermoplastic Rubber

| Spin No. | 33 |
|---|---|
| Percent Ethylene | 60–65 |
| Percent Propylene | 35–40 |
| Melt Temperature (° C) | 360 |
| Quench Conditions (R.T.) | water |
| Take-up Speed, mpm | 17.8 |
| Fiber Dimensions: | |
| OD, microns | 522 |
| ID, microns | 237 |
| Initial $P_A$ (70° ) | $.13 \times 10^{-4}$ |
| Initial P (70° ) | $11 \times 10^{-8}$ |

EXAMPLE 6

The permeability rates of polyethylene hollow fibers have been found to undergo deterioration during aging when stored under inert conditions such as under water and when aged under conditions of use. Such deterioration is pronounced and rapid, ranging from a loss to only about 25% of initial P in as little as 2 days for an unannealed polyethylene hollow fiber to a 120% loss of initial P in 10 days for a preannealed polyethylene hollow fiber. Table VI below sets out the results with both unannealed and annealed hollow fibers of polyethylene when aged in an aqueous solution of 3% by weight phenol at 70° C for the indicated times.

TABLE VI

| Exposure time (Hours) | P × 10⁸ Unannealed | Unannealed | Annealed[a] |
|---|---|---|---|
| 0 | 1.0 | 1.0 | 2.0 |
| 50 | 0.23 | 0.23 | — |
| 120 | — | — | 1.0 |
| 240 | — | — | 0.85 |

[a]Annealed in a bath of 3% phenol for 2 hours at 80° C at constant length prior to exposure.

EXAMPLE 7

In contrast to the aging results set out in Table VI above, the hollow fibers of the present invention have been found to suffer a much smaller and slower decline in permeation rate and, in the case of a hollow fiber of ethylene-propylene copolymer rubber, no decline at all. The results of determination of intrinsic permeabilities P × 10⁸ for hollow fibers produced from an ethylene-vinyl acetate copolymer of 12 wt. % vinyl acetate and an ethylene-propylene copolymer rubber when aged in a 3% by wt. aqueous solution of phenol for the indicated number of days are set out in Table VII below.

TABLE VII

Phenol Permeability of Ethylene Copolymers (Test in 3% Phenol, 70° C)

| Age (Days) | P × 10⁸ Et/VA Fiber | Et/Prop.Fiber |
|---|---|---|
| 0 | 91 | 11 |
| 1 | 80 | — |
| 2 | 72 | — |
| 4 | 53 | — |
| 5 | — | 15 |
| 10 | 52 | — |
| 12 | — | 15 |
| 22 | 48 | — |

The hollow fibers of the present invention have also been found to demonstrate satisfactory physical properties under operating conditions.

EXAMPLE 8

Table VIII below sets forth the results of determinations of yield stress ($\sigma_y$) and modulus of elasticity (E × 10⁻⁸) of several hollow fibers of ethylene-vinyl acetate copolymers of varied vinyl acetate content which have been preannealed at 80° C for two hours unrestrained except when otherwise indicated prior to testing them under operating conditions in 3% aqueous solutions of phenol at the temperature indicated. It has been found that a yield stress of at least about 3.5 kg/cm² at operating temperatures is required for practical use of hollow fibers in dialysis and other relatively low pressure separations processes, while optimum values for yield stress under conditions of use are generally about 7.7 kg/cm² or more. Although all the fibers tested demonstrated yield strengths of 7.7 kg/cm² or greater under the conditions of the test, sample F would be deemed of borderline value because of its low operating temperature and it is not representative of the present invention.

TABLE VIII

| Sample | A | B | C | D | E | F |
|---|---|---|---|---|---|---|
| Ethylene % | 90 | 90 | 90 | 88 | 82 | 72 |
| Annealing Temp. ° C | 80 | 80 | 80 | 80 | 65 | 50 |
| Test Temp. ° C | 50 | 70 | 80 | 70 | 60 | 50 |
| $\sigma_y$ (kg/cm²) | 95.4 | 52.1 | 46.1 | 16.5 | 7.7 | 14.4 |
| E×10⁻⁸ (dynes/cm²) | 6.4 | 3.5 | 3.0 | 1.3 | 0.73 | 0.56 |

EXAMPLE 9

This example demonstrates the satisfactory operation of the ethylene copolymer hollow fibers of the present invention under operating conditions. A test loop of hollow fibers of 88% ethylene-12% vinylacetate copolymer having an OD of 206 microns and ID of 131 microns was prepared as above described containing 120 individual fibers with an epoxy resin seal protected by an air space and a silicone rubber protective dam. The test loop was suspended in a slip stream of an industrial waste water line having a pH of about 2.0 to 2.5 and containing phenols in approximately the following concentrations:

| | Parts per Million |
|---|---|
| Phenol | 15,600 |
| Cumylphenol | 180 |
| Nonylphenol | 20 |

The bores of the fiber test loop were continually fed an aqueous solution of about 13% potassium hydroxide by weight under positive pump pressure. The permeability coefficient of the test loop fibers to phenol at operating temperature of about 60° C was determined at intervals throughout the thirty day test period by sampling the bore effluent and analyzing the potassium phenate content. The results of these permeability coefficient determinations set out in Table IX below show that the ethylene copolymer hollow fibers withstand the waste stream constituents and function to separate phenols therefrom over an extended period.

TABLE IX

| Days of Operation | $P\left(\dfrac{\text{cc-cm}}{\text{sec. cm}^2 \Delta VF}\right) \times 10^8$ |
|---|---|
| 1 | 20.2 |
| 2 | 11.1 |
| 3 | 16.0 |
| 6 | 29.9 |
| 8 | 28.5 |
| 12 | 51.6 |
| 16 | 31.1 |
| 20 | 25.2 |
| 24 | 36.8 |
| 28 | 57.8 |
| 30 | 76.2 |

We claim:

1. A hollow fiber membrane consisting of a copolymer of ethylene with from 5 to 20 weight percent of a copolymerized vinyl monomer having an outside diameter of from 50 to 1000 microns, a wall thickness having a ratio of from 0.1 to 0.4 of said outside diameter and having a intrinsic permeability of phenol determined in a dilute aqueous solution of phenol at about 70° C of from about 5 to about 100 × 10⁻⁸ cc's per cm thickness per second per square centimeter per volume fraction differential.

2. A hollow fiber membrane of claim 1 wherein the copolymerizable vinyl monomer is selected from the group consisting of vinyl esters, acrylic acid, methacrylic acid, acrylic esters, methacrylic esters and copolymerizable monoolefins.

3. A hollow fiber membrane of claim 1 wherein the copolymer of ethylene is a copolymer of ethylene and vinyl acetate.

4. A hollow fiber membrane of claim 1 wherein the copolymer of ethylene is a copolymer of ethylene and acrylic acid.

5. A hollow fiber membrane of claim 1 wherein the copolymer of ethylene is a copolymer of ethylene and ethyl acrylate.

6. A hollow fiber membrane of claim 1 wherein the copolymer of ethylene is a copolymer of ethylene and propylene.

7. A hollow fiber membrane of claim 1 wherein the wall thickness is from 10 to 150 microns.

8. A hollow fiber membrane of claim 1 wherein the net permeability for phenol from an aqueous solution of phenol is from about 0.25 to about $4.0 \times 10^{-4}$.

9. A hollow fiber membrane of claim 1 wherein the yield stress is greater than 3.5 Kg/cm$^2$ at a temperature of 50° C.

10. The process for the separation of phenols from aqueous solutions of phenols comprising contacting an aqueous solution of phenols with a first surface of a hollow fiber membrane consisting of a copolymer of ethylene and from 5 to 20 weight percent of a copolymerized vinyl monomer, said membrane having an intrinsic permeability to phenol determined in a dilute aqueous solution of phenol at about 70° C of from about 5 to about $100 \times 10^{-8}$ cc's per cm thickness per second per square centimeter per volume fraction differential, maintaining a second and opposite surface of said hollow fiber membrane at a lower chemical potential than said first surface, permeating a portion of said phenols into and through the hollow fiber membrane, and withdrawing at the second surface phenols at a higher concentration than the phenols concentration in said aqueous solution.

11. The process of claim 10 wherein the copolymerizable vinyl monomer is selected from the group consisting of vinyl esters, acrylic acid, methacrylic acid, acrylic esters, methacrylic esters and copolymerizable monoolefins.

12. The process of claim 10 wherein the copolymer of ethylene is a copolymer of ethylene and vinyl acetate.

13. The process of claim 10 wherein the copolymer of ethylene is a copolymer of ethylene and acrylic acid.

14. The process of claim 10 wherein the copolymer of ethylene is a copolymer of ethylene and ethyl acrylate.

15. The process of claim 10 wherein the copolymer of ethylene is a copolymer of ethylene and propylene.

16. The process of claim 10 wherein the hollow fiber membrane has a wall thickness of from 10 to 150 microns.

17. The process of claim 10 wherein said hollow fiber membrane has a net permeability for phenol of from about 0.25 to $4.0 \times 10^{-4}$.

18. The process of claim 10 wherein the second surface of said membrane is maintained at a lower chemical potential by contacting said second side with a solution of a complexing agent or reagent which reacts with said phenols.

19. The process of claim 18 wherein said reagent is an aqueous solution of an alkali metal hydroxide.

20. The process of claim 18 wherein said reagent is sodium hydroxide.

21. The process of claim 18 wherein said reagent is potassium hydroxide.

22. The process of claim 18 wherein said aqueous solution of phenols is maintained at a pH below about 5 and said solution of a complexing agent or reagent is maintained at a pH above about 10.

* * * * *